United States Patent [19]
Osther et al.

[11] Patent Number: 5,264,342
[45] Date of Patent: Nov. 23, 1993

[54] METHOD FOR DETERMINING THE SENSITIVITY AND/OR SPECIFICITY OF AN ASSAY SYSTEM FOR DETECTING ANTIBODIES

[75] Inventors: Kurt B. Osther, San Diego, Calif.; Gottfried H. Kellermann, Osceola, Wis.

[73] Assignee: Verigen, Inc., Hopkinton, Mass.

[21] Appl. No.: 962,603

[22] Filed: Oct. 16, 1992

Related U.S. Application Data

[63] Continuation of Ser. No. 611,307, Nov. 9, 1990, which is a continuation-in-part of Ser. No. 192,241, May 10, 1988, Pat. No. 5,008,183.

[51] Int. Cl.$^5$ .................... C12Q 1/70; C12Q 1/00
[52] U.S. Cl. ........................ 435/5; 435/7.1; 435/967; 436/16; 436/547; 530/387.1; 530/389.1; 530/389.4; 530/389.5
[58] Field of Search ............ 435/57.1, 967; 436/16, 436/547; 425/858; 530/387.1, 389.1, 389.4, 389.5

[56] References Cited
U.S. PATENT DOCUMENTS

| | | |
|---|---|---|
| 4,007,008 | 2/1977 | Becker et al. .................... 436/16 |
| 4,022,878 | 5/1977 | Gross .............................. 436/547 |
| 4,643,896 | 2/1987 | Asakura et al. ................... 424/88 |
| 4,816,253 | 3/1989 | Likhite ............................ 424/92 |
| 5,006,464 | 4/1991 | Chu et al. ........................ 435/7.1 |
| 5,008,183 | 4/1991 | Osther ............................ 436/547 |

OTHER PUBLICATIONS

Ed Hurlow and David Lane, "Antibodies, A Laboratory Manual" 1988 Cold Spring Harbor Lab. pp. 93, 98, 127.

Primary Examiner—Christine M. Nucker
Assistant Examiner—Chris Dubrole
Attorney, Agent, or Firm—Barnhard, Elizabeth M.; Bryan Cave

[57] ABSTRACT

A method for determining the sensitivity and/or specificity of assays that detect the presence or absence of antibodies to viral and/or other microbial infective agents using porcine seroconversion panels, and production of the seroconversion panels is provided.

19 Claims, 2 Drawing Sheets

HTLV-I IgM SEROCONVERSION PANEL

METHOD FOR DETERMINING THE SENSITIVITY AND/OR SPECIFICITY OF AN ASSAY SYSTEM FOR DETECTING ANTIBODIES

This is a continuation of U.S. application Ser. No. 07/611,307, filed Nov. 9, 1990, which is incorporated herein by reference, which is a continuation-in-part of U.S. application Ser. No. 07/192,241, filed May 10, 1988 (issued as U.S. Pat. No. 5,008,183 on Apr. 16, 1991), which is incorporated by reference.

TECHNICAL FIELD

The present invention relates to the use of porcine seroconversion panels for determining the sensitivity and/or specificity of assay systems for detecting the presence or absence of antibodies to viral and/or other microbial infective agents, and to a method of producing the porcine seroconversion panels. In particular, the invention pertains to the use of porcine immune IgG, porcine immune IgA, and porcine immune IgM seroconversion panels.

BACKGROUND OF THE INVENTION

Assay systems capable of detecting the presence or absence of antibodies generated in response to the presence of antigens are well known. Such assay systems have proved useful in, inter alia, the diagnosis of various diseases. For example, viral infections, such as AIDS (acquired immune deficiency syndrome) and CMV (cytomegalovirus) may be diagnosed with assays which detect the presence of viral antibodies including immunoglobulins IgG, IgA, and IgM, in patients suspected of having these diseases. Examples of such assay systems which employ antigen-antibody binding include ELISA, Western Blot, Quick Western Blots (U.S. Pat. Nos. 4,816,387 and 4,855,235) and RIA. Such diagnostics uniformly include controls to insure the integrity of the test system.

Typically, the diagnostics have both positive and negative controls. The positive control provides pertinent information concerning the activity of the test system, i.e., that reactive antibodies specific to the antigens used in an antibody test system are bound to the antigens (indicating that the antigens used in the test system are working properly), and that the anti-immunoglobulin used to detect the bound immunoglobulin is working. In the case of an ELISA system the anti-immunoglobulin may be labeled with an enzyme (conjugate) which activates a substrate added to the system to give a chromogen reaction; in this case the positive control indicates whether the conjugate has reacted, and whether the substrate has worked properly as an activated chromogen. A negative control provides information about the absence of reactive antibodies specific to the particular antigens used in a test system. It also provides information as to the reaction level, determined by the signal used in a particular test, at which a specimen may be considered negative.

The cut-off point in a particular test is often based upon the relative value obtained by a positive control and/or by the negative control. An acceptable detection range obtained by the controls utilized with a particular type of test kit is specifically designed and titrated for that type of kit. The positive control "value" obtained in a particular test system affects the sensitivity of that test system; the negative control "value" affects the specificity of the test system.

Seroconversion panels are conventionally used to estimate the sensitivity and specificity of diagnostic tests or assay systems. A seroconversion panel is made by drawing consecutive blood samples over time from a donor infected with a known microbial organism. The day that the blood sample is taken is the time point for that sample. The blood serum contains antibodies to the microorganism such as IgG, IgA, and IgM. Seroconversion panels containing antibodies to retroviruses such as HIV-1, HIV-2, HTLV-1, and HTLV-II, and to other microorganisms such as toxoplasma, cytomegalovirus, Borellia b. (LYME), and Rubella, have been obtained by following certain plasmaphoresis donors or by repeatedly drawing blood samples from high risk individuals. The collected blood from each drawing is then tested for the presence of antibodies to the microbial organism and aliquotted in minute volumes, typically 100 to 250 microliters (ul) and stored for future use. The consecutive time point samples as a group constitute a seroconversion panel.

Notably, the supply of antibodies is scarce and uncertain and the quality and characteristics of the antibody varies from donor to donor. Further, as more successful therapies become known and used, fewer seropositive donors will be available, and thus the required antibody even more difficult to obtain.

In the case of AIDS patients it has been found that the condition of patients who donate blood or are subjected to plasmaphoresis deteriorates rapidly. Therefore, obtaining AIDS Positive blood or plasma from patients as a source of antibody for use in a seroconversion panel should be avoided.

The previously mentioned assay systems detect infection indirectly by detection of the presence or absence of antibodies. Seroconversion panels disclose how early an infection can be detected.

These assay systems detect the presence or absence of IgG (immunoglobulin G). Such assays only allow "controlled" detection (measurement defined by use of anti-IgG conjugate and of antibody positive control) of the presence of IgG in blood and body fluids directed to antigens used in the test systems. The appearance of detectable IgG directed to antigens in an infected/immunized individual does not occur until 30–40 days after initial infection in many instances. The IgG class antibodies are often present for months or years after infection/immunization.

The presence of circulating IgG directed to immunizing antigens during the course of an infection (or after immunization) is preceded by the presence of circulating IgM and/or IgA antibodies directed towards the antigens/immunogens. IgM and/or IgA antibodies directed to antigens in an infected/immunized individual are often present in detectable quantities as early as 14 days (or earlier) after the infection/immunization. The IgM class antibodies gradually lose titer 30–35 days after initial infection/immunization.

It is widely recognized that diagnostics which can detect antibodies other than IgG are desirable. For example, it is known that generally after confrontation with a foreign body, the human immune system responds by generating antibodies against the foreign body or antigen. It is believed that IgM and/or IgA, not IgG is produced first. As can be appreciated, assays capable of detecting IgM and/or IgA will facilitate early detection of numerous diseases. IgM is, however, a relatively short-lived antibody. While it may be produced shortly after infection, IgM levels fall, eventually below detectable levels, as IgG is produced in increasing amounts. Because IgM has a short life span, IgM levels are typically below detectable levels before many diseases are even diagnosed. Therefore, IgM is not readily obtainable from seropositive donors and a dependable, reliable source of this important antibody is needed.

Seroconversion panels can be used to test each manufactured batch of assay systems or diagnostic test kits to ensure that the assay system performs with the same high sensitivity and specificity each time it is to be released for distribution. Test laboratories which use such assay systems or test kits can use seroconversion panels to ensure that the laboratories are performing high quality testing.

The present invention overcomes the previously mentioned disadvantages because it provides the ability to produce the desired seroconversion panels, i.e., porcine IgG, IgA, and IgM antibody seroconversion panels. In accordance with the present invention, there is provided a method of using the porcine seroconversion panels to determine the sensitivity and/or specificity of assay systems detecting antibodies to viral and/or microbial infective agents.

SUMMARY OF THE INVENTION

The present invention provides a use of porcine seroconversion panels for determining the sensitivity and/or specificity of assays that detect the presence or absence of antibodies which bind to viral and/or other microbial antigens and production of porcine seroconversion panels. In particular, the invention is useful in connection with assays in which predetermined antigens are sequentially contacted with a biological fluid and positive control comprising antibodies to the antigens for times and under conditions sufficient for the antigens and any antibodies in the biological fluid, and the antigens and antibodies in the positive control, to form antigen-antibody complexes, and the formation of the complexes is therewith detected. The sensitivity and/or specificity of the assay is determined by using seroconversion panels containing human antibodies to the antigens instead of the biological fluid, the improvement comprising the use of seroconversion panels containing porcine antibodies which bind to the antigens and react to anti-human antibody.

The present invention can be used to provide seroconversion panels containing known titers of antibodies to predetermined antigens. The sensitivity and/or specificity of different assays for detecting antibodies to the predetermined antigens can be compared by using each assay to measure the presence of the antibodies in the seroconversion panels and comparing the measurements. The comparison of the measurements obtained by the different assays will show which assay is more sensitive and/or more specific.

It is presently preferred to use porcine immune IgG, IgM, and/or IgA seroconversion panels.

A further advantage of the present invention is that porcine seroconversion panels can be produced with antibodies reactive to predetermined antigens of only one viral or other microbial infective agent or of a plurality of viral or other microbial infective agents. No such manipulation is possible with human donor derived seroconversion panels.

A further advantage of the present invention is that a porcine seroconversion panel containing a plurality of antibodies to a group of microorganisms, such as human retroviruses HIV-1, HTLV 1, HIV-2 and HTLV-II can be used by makers of assay systems to develop and control the sensitivity and specificity of their assay systems to detect any one of the plurality of antibodies in the same assay. Such an assay would enable one test to be performed on a sample instead of a series of individual assays to detect one antibody at a time. If a positive reaction is obtained, then the sample can be tested further, if necessary, to determine the exact antibody that is reacting. For example, blood banks which screen donated blood for the presence of AIDS antibodies, could use an assay containing antigens to HIV-1, HTLV-1, HTLV-II and HIV-2, instead of four individual assays using only one antigen. If the test sample is not reactive, then no further testing is required. If the test sample is reactive, then the sample could be further tested, if necessary, in assays using one of the four antigens to identify the viral antigen to which the test sample is reacting.

DETAILED DESCRIPTION OF THE INVENTION

Figure 1:
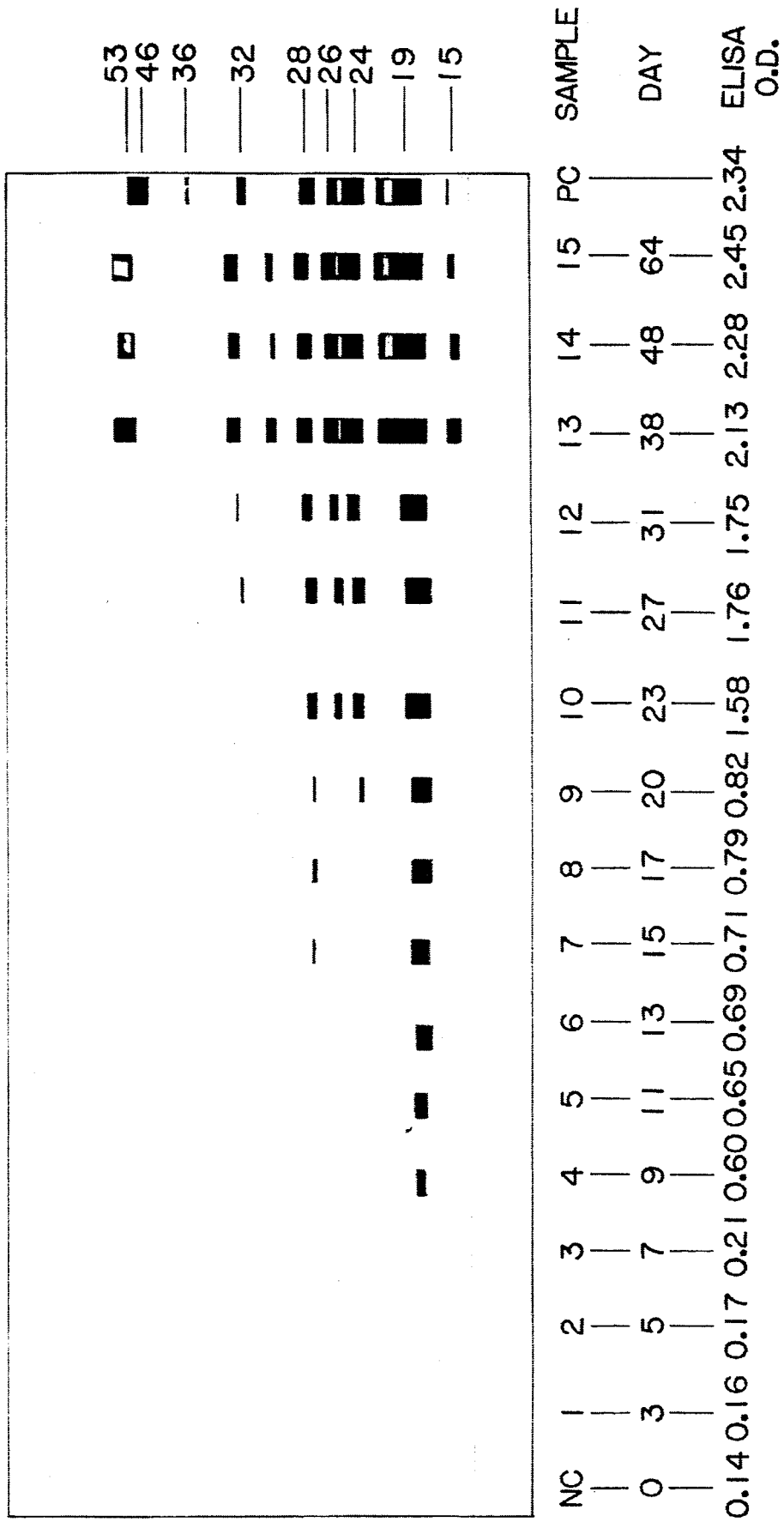
FIG. 1 presents the results of a Western Blot assay measuring the presence of HTLV-1 IgG in a porcine seroconversion panel and the corresponding results of the ELISA assay on the same panel. Samples are numbered 1 to 15, the negative control is identified as "NC", and the positive control is identified as "PC". The time point is listed below the sample. The ELISA optical density (O.D.) reading of the sample is presented below the time point. The Western Blot result for a sample is shown above the sample number with protein identifying band numbers 15, 19, 24, 26, 28, 32, 36 and 53 and glycoprotein identifying band number 46 presented in numerical order to the right of the PC sample. The band numbers are used to identify the band in the sample that aligns with the corresponding band number in the right hand column.
Figure 2:
FIG. 2 presents the results of a Western Blot assay measuring the presence of HTLV-1 IgM in a seroconversion panel and the corresponding results of the ELISA assay on the same panel illustrated in the same manner as FIG. 1.

In accordance with the present invention, porcine seroconversion panels are obtained by immunizing a pig with viral or other microbial material against which it is desired to raise specific antibodies and drawing sequential time point samples of antibody-containing blood from the immunized pig, with aliquots of these time point samples being used to make seroconversion panels. Examples of suitable immunizing agents include HIV-1, HIV-2, HTLV-1, HTLV-II, CMV, LYME, toxoplasma, Rubella, and Epstein-Barr virus. Of course, other immunizing agents as may be known to those skilled in the art are also useful.

The immunization begins with a first vaccination of the animal with a preparation comprising 10–500 micrograms (ug) of viral or microbial lysate or selected portions of the viral core or envelope proteins or of the microbial core or membrane Proteins. Viral material is generally solubized in Triton X-100; SDS, (sodium dodecyl sulfate), mercaptoethanol, and/or NP 40 (Nonidet P40 detergent, nonionic detergent), and suspended in phosphate buffered saline (PBS), pH 7.2-7.4. It is preferred to solubilize the viral material with 0.1% NP 40, a mild detergent, and to heat the solubilized viral material up to 30 minutes at 50°–60° C., to elicit a slight unfolding of the outer shell or envelope proteins which solubilized viral material is then diluted with 1% SDS. The first injection contains an adjuvant; Freund's complete adjuvant (FCA) is preferred for this purpose. Of course, other adjuvants known to those skilled in the art may also be used. The first vaccination typically comprises a total volume of 2 ml, one ml of viral material in buffer plus one ml of adjuvant. The viral material and adjuvant should be thoroughly mixed immediately prior to injection. In a preferred embodiment, the first vaccination contains 50–100 ug of viral material in 1.0 ml of 1% SDS mixed with 1.0 ml of FCA.

Booster immunizations are generally prepared with adjuvant and typically contain 10–500 ug of viral proteins, preferably from about 50–100 ug per injection in PBS, pH 7.2–7.4. It is preferred that booster immunizations are prepared with Freund's incomplete adjuvant. It is further preferred that the booster immunization contains 50–100 ug of viral material solubilized in 0.1% NP 40, heated for up to 30 minutes at 50°–60° C., and diluted with 1% SDS. Booster injections begin from about 7 to 30 days after the initial vaccination and every 7 to 30 days thereafter until the desired number of samples needed for the seroconversion panel is obtained. It is preferred that the first booster injection be given twenty-four hours after the first vaccination. Preferably, up to four booster immunizations are given. It is further preferred that the fourth or final booster immunization be prepared with Freund's incomplete adjuvant and with viral lysate solubilized in 1% SDS and heated for up to 40 minutes at 65°-75° C. to elicit unfolding of the outer shell or envelope proteins and to expose the interior or core proteins, thereby allowing an immunoresponse to these interior proteins.

A first blood sample is generally drawn and tested prior to the initial vaccination to establish a baseline antibody level. It is presently preferred to vaccinate by intracutaneous or subcutis injection, but other modes of administration, such as intramuscular injection may be used. The vaccination site is preferably the side of the neck, typically injecting three to four different locations. Vaccination on the neck is considered to yield higher antibody titers, but other vaccination sites as are known to those skilled in the art are suitable for raising the desired immune antibody.

Blood is collected from the immunized animal by consecutive bleedings after the first immunization, preferably every 2 to 3 days, until a sufficient number of consecutive blood samples, preferably 8 to 16 time points, are obtained for the desired seroconversion panel. The titer of the desired antibody of each blood sample or serum extracted therefrom is measured. Once the timing and frequency of blood drawings (time points) is established for the particular immunogen being used, a multiple number of animals can be immunized. The animal is sacrificed and the blood collected at only one time point, each animal's time point being different and including an animal for a baseline time point. The total collected blood of one animal would represent one time point sample. The advantage is that large amounts of antibody-containing blood for a particular time point in a seroconversion panel can be readily obtained.

It is preferred to use serum from the immunized animal in a seroconversion panel. However, whole blood, plasma or any other form of antibody as may be known to those skilled in the art may be used. Before use, it is preferred to filter and sterilize the blood or serum and then freeze aliquots for later use; alternatively, the serum may be freeze-dried or dried or fractionated to enrich the IgG, IgM or IgA fractions.

The previously described method can be used to produce seroconversion panels containing antibodies against several viruses including HIV-1, HIV-2, HTLV-1, HTLV-II, cytomegalovirus, Epstein-Barr virus, toxoplasma, and hepatitis B virus. It is also considered within the scope of the invention to produce seroconversion panels containing antibodies against a variety of other microorganisms such as Rubella, Borrelia b. (LYME), E. coli, salmonella, tetanus, streptococcus and Neisseria.

The previously described method can be used to produce antibodies for seroconversion panels in animals other than pigs, including rabbits, goats, mice, rats, sheep, cows, horses, and monkeys.

The following examples are considered illustrative of the present invention.

EXAMPLE 1

Porcine Immune IgG and IgM Against HTLV-1

An immunogen for injection was prepared with inactivated HTLV-1 lysate, containing proteins (p) 19, 24, 26, 38, and glycoprotein (gp) 46. The HTLV-1 lysate, present in a concentration of 1 mg/ml in 0.1% NP 40 (a nonionic detergent), 0.5 m NaCl and TNE buffer (29.2 g/l NaCL, 1.2 g/l Tris, and 0.37 g/l EDTA), was heated for 30 minutes at 56° C. One hundred ul of the HTLV-1 viral lysate were diluted with 900 ul of 1% SDS. Shortly before injection, this diluted viral lysate was mixed with 1.0 ml Freund's comple adjuvant (FCA) to make the immunogen.

Just prior to injection, day 0, 20-50 ml of blood were drawn from the ear vein of a four month old female Yorkshire mixed-breed pig and tested for the presence of IgG and IgM antibodies to HTLV-1. This was the baseline sample. The pig was then immunized by subcutis or intracutaneous injections at four different sites in the left side of the neck.

Booster injections contained 100 ul of HTLV-1 viral lysate in 900 ul of 1% SDS mixed with 1 ml Freund's incomplete adjuvant (FIA). The first booster was administered twenty-four hours later (day 1), a second booster 16 days later (day 17), and a third booster 14 days later (day 31). Seventeen days later (day 48), a fourth booster was prepared where 100 ul of HTLV-1 viral lysate diluted in 900 ul 1% SDS was first heat treated for 40 minutes at a temperature from 65° to 70° C. and then mixed with 1 ml FIA. The pig was vaccinated with this fourth booster on day 48. The pig received a total of five injections.

In addition to the baseline blood sample, 20 to 50 ml blood samples were drawn from an ear vein on days 3, 5, 7, 9, 11, 13, 15, 17, 20, 23, 27, 31, 38, 48 and 64. A total of sixteen samples of blood were drawn when the baseline is included.

Each blood sample, a positive control, and a negative control was separately tested for the presence of IgG antibodies to HTLV-1 and IgM antibodies to HTLV-1 using a Western Blot technique. The appearance and relative strength of proteins bands were studied. Antibody titer for each sample was determined using an ELISA assay. Serum was collected from each of the sixteen blood samples, aliquotted in minute volumes of 100-250 ul, labelled, and stored for use in seroconversion panels containing at least one aliquot from each of the sixteen samples.

EXAMPLE 2

Porcine Immune IgG and IgM Against HIV-1

The method of Example 1 was used except that inactivated HIV-1 viral lysate was used instead of inactivated HTLV-1 viral lysate. The HIV-1 lysate contained p18, p24, p31, gp41, gp48, p53, p56, p64, gp110, gp120, and gp160.

EXAMPLE 3

Sensitivity/Specificity Testing of Western Blot for IgG Against HTLV-1 Using Porcine HTLV-1 Seroconversion Panel DuPont Western Blot strips precoated with HTLV-1 antigen (Lot #R0153 H-91) were tested for sensitivity and specificity using a porcine HTLV-1 seroconversion panel from Example 1. The aliquots of the seroconversion panel were diluted 1 to 30 with PBS Tween. To a single Western Blot strip, 2 ml of one of the diluted aliquots of serum, for example, day 1, was added and incubated for 30 minutes at room temperature on a rocking platform. This step was simultaneously repeated for all of the diluted aliquots of serum of the seroconversion panel and positive and negative controls. After incubation, the fluid was removed and each strip washed sequentially four times with 3 ml of PBS Tween.

Subsequently, 2 ml of a conjugate of goat anti-human IgG, gamma-chain, conjugated with alkaline phosphatase (Calbiochem, Lot #040090), diluted 1 to 500 in PBS Tween was added to each strip and incubated for 30 minutes at room temperature. The fluid was removed and each strip was washed sequentially three times with 3 ml PBS Tween and then one time with 3 ml 0.1M carbonate buffer (pH 9.2).

To each strip 2 ml of chromogen, 1:1 nitrobluetetrazolium salt (NBT) to 5-bromo-4-chloro-3-indolylphosphate (BCIP) was added and incubated for 10 minutes at room temperature. The reaction was stopped by adding 50 ul of 2N sulfuric acid. Each strip was then put in distilled water for five minutes, dried, and then the protein and glycoprotein bands were read. The strips are shown in FIG. 1.

On day 9, one protein band, p19, appeared. On day 23, four protein bands appeared, p19, p24, p26, and p28, indicating a higher titer of IgG. At day 38, 8 proteins and 1 glycoprotein appeared, p15, p19, p24, p26, p28, p32, p36, p53, and gp46, indicating a high titer of IgG, which remained constant through day 64.

EXAMPLE 4

Sensitivity/Specificity Testing of Western Blot for IgM Against HTLV-1 Using Porcine HTLV-1 Seroconversion Panel The method of Example 3 was repeated except that the conjugate used was 2 ml of goat anti-human IgM, mu-chain, conjugated with alkaline phosphatase (Calbiochem, Lot #041890) diluted 1:500 in PBS Tween. The resulting strips are shown in FIG. 2.

In contrast with FIG. 1, FIG. 2 shows the presence of IgM by day 9 with the appearance of three protein bands, p19, p26, and p28. At day 23, a high titer of IgM is indicated by the appearance of protein bands at p15, p19, p24, p26, p28, p32, and p36. This remains fairly constant until day 48 where, in contrast to the IgG seroconversion panel of Example 3, the IgM titer declines as shown by the decreasing number of protein bands.

EXAMPLE 5

Sensitivity Testing Of ELISA Assay For IgG Against HTLV-1 In Porcine Seroconversion Panels The sensitivity of the DuPont HTLV-1 ELISA test kit was tested by measuring the presence of IgG in the porcine seroconversion panel of Example 1. Positive and negative controls were also measured. The ELISA assay was carried out in accordance with the manufacturer's instructions. The optical density (O.D.) readings are presented in FIG. 1. On day 9, a slight increase in the O.D. reading, 0.60, appears when compared to the negative control O.D. reading of 0.14. On day 23, there is a marked increase to 1.58, indicating a higher titer of IgG. On day 38, there is another significant increase to 2.13, indicating a high titer of IgG. From day 38 to day 64, the titer of IgG is fairly constant.

EXAMPLE 6

Sensitivity Testing Of ELISA Assay for IgM Against HTLV-1 In Porcine Seroconversion Panels The sensitivity of the DuPont HTLV-1 ELISA test kit was tested by measuring the presence of IgM in the porcine seroconversion panel of Example 1. Positive and negative controls were also measured. The ELISA assay was carried out in accordance with the manufacturer's instructions with two modifications.

Prior to starting the ELISA assay, the seroconversion panel was pretreated to remove IgG, which interferes with the ELISA measurement of IgM. Each aliquot of serum from the seroconversion panel was diluted 1:10 in PBS Tween. The amount of IgG present in the sample was estimated and an equivalent amount of Protein G (Pierce, Immuno Pure Immobilized Protein G) was mixed in with the diluted serum and incubated at 37° C. for 30 minutes. The diluted sample was then centrifuged for 5 minutes at 10,000 rpm. The supernatant was removed and then used in the ELISA assay.

The second modification was the replacement of the IgG conjugate of the test kit with an IgM conjugate, using goat anti-human IgM, mu-chain, conjugated with alkaline phosphatase (Calbiochem, Lot #041890) which was diluted 1:4000 in PBS Tween.

The resulting O.D. readings are presented in FIG. 2.

In contrast to Example 5, on day 9, on O.D. reading of 1.22 was obtained, indicating a high titer of IgM. On day 23, the titer peaked, giving an O.D. reading of 1.75. On day 38, an O.D. reading of 1.17 indicated the titer was decreasing. The titer continued to decrease as shown by the decreasing O.D. values.

These examples demonstrate the utility of porcine seroconversion panels in testing the sensitivity and/or specificity of different assays which detect the presence or absence of antibodies to viral and/or other microbial infective agents.

While the preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, of the scope of the invention being defined by the following claims.

We claim:

1. A method for determining the sensitivity and/or specificity of an assay for detecting the presence or absence of human antibodies which bind to predetermined antigens of viruses or other microorganisms, comprising the steps of:
   (a) preparing a seroconversion panel of porcine immune antibodies reactive to one or more predetermined antigens of viruses or other microorganisms, said seroconversion panel comprising a plurality of time point antibody-containing blood samples sequentially drawn from a pig immunized with said antigens in which the reaction of the porcine antibodies to said antigens is similar to the reaction of the human antibodies to said antigens;
   (b) contacting an aliquot of a sample of one or more predetermined antigens from an assay whose sensitivity and/or specificity is to be determined with the plurality of porcine time point antibody-containing blood samples of the seroconversion panel for times and under conditions sufficient for the predetermined antigens and porcine antibodies to form antigen-porcine antibody complexes; and
   (c) detecting the formation of any antigen-porcine antibody complexes in step (b) by simultaneously contacting an anti-human antibody with any antigen-porcine antibody complex as formed, for times and under conditions sufficient for any antigen-porcine antibody complexes formed in step (b) to react with the anti-human antibody.

2. The method of claim 1, wherein the seroconversion panel comprises 8 to 16 sequential time point antibody-containing blood samples drawn from a pig.

3. The method of claim 1, wherein the porcine immune antibodies comprise IgG, IgM or mixtures thereof.

4. The method of claim 1, wherein the porcine immune antibodies comprise an antibody to a human retrovirus causing acquired immune deficiency syndrome or AIDS related complex (ARC).

5. The method of claim 4, wherein the porcine immune antibodies comprise IgG, IgM or mixtures thereof.

6. The method of claim 1, wherein the porcine immune antibodies comprise an antibody to HTLV-1.

7. The method of claim 6, wherein the porcine immune antibodies comprise IgG, IgM or mixtures thereof.

8. The method of claim 1, wherein the porcine immune antibodies are antibodies to a human retrovirus causing acquired immune deficiency syndrome or AIDS related complex (ARC) and to HTLV-1.

9. The method of claim 8, wherein the porcine immune antibodies comprise IgG, IgM or mixtures thereof.

10. The method of claim 1, wherein the porcine immune antibodies comprise an antibody to cytomegalovirus (CMV).

11. The method of claim 10, wherein the porcine immune antibodies comprise IgG, IgM or mixtures thereof.

12. The method of claim 1, wherein the porcine immune antibodies comprise an antibody to Borrelia b. (LYME).

13. The method of claim 12, wherein the porcine immune antibodies comprise IgG, IgM or mixtures thereof.

14. The method of claim 1, wherein the porcine immune antibodies comprise an antibody to Rubella.

15. The method of claim 14, wherein the porcine immune antibodies comprise IgG, IgM or mixtures thereof.

16. The method of claim 1, wherein the porcine immune antibodies comprise an antibody to toxoplasma.

17. The method of claim 16, wherein the porcine immune antibodies comprise IgG, IgM or mixtures thereof.

18. The method of claim 1, wherein the porcine immune antibodies are selected from the group of antibodies to HIV-1, HIV-2, HTLV-1, HTLV-II, cytomegalovirus (CMV), and Epstein Barr virus.

19. The method of claim 18, wherein the porcine immune antibodies comprise IgG, IgM or mixtures thereof.

* * * * *